United States Patent [19]

Berger et al.

[11] Patent Number: 4,624,262

[45] Date of Patent: Nov. 25, 1986

[54] APPARATUS AND PROCESS FOR VERY RAPIDLY MEASURING THE HEART BEAT RATE

[75] Inventors: Henri Berger, 90 Bld de Latour Maubourg, 75007 Paris; Didier Lapeyre, Pacy sur Eure, both of France

[73] Assignee: Henri Berger, Paris, France

[21] Appl. No.: 674,922

[22] Filed: Nov. 26, 1984

[30] Foreign Application Priority Data

Nov. 25, 1983 [FR] France .................... 83 18856

[51] Int. Cl.$^4$ .............................................. A61B 5/02
[52] U.S. Cl. ................................................ 128/689
[58] Field of Search ............... 128/687, 689, 690, 639

[56] References Cited

U.S. PATENT DOCUMENTS

| 2,572,380 | 10/1951 | Rice | 128/687 |
| 4,239,048 | 12/1980 | Steuer | 128/690 |
| 4,350,164 | 9/1982 | Allain, Jr. | 128/639 |

*Primary Examiner*—William E. Kamm
*Attorney, Agent, or Firm*—Larson and Taylor

[57] ABSTRACT

An apparatus whose case (12) has advantageously the general shape of a pen, for the external measurement of the heart beat frequency of a patient, comprising: at least one dynamometer (10) intended, during operation, to be held pressed in the anatomical gutter of the radial artery with a substantially constant force less than that created by the systolic pressure of the blood flow in the radial artery; means for detecting the maxima of the flow; computing means for determining the heart beat rate; and means (11) for displaying this rate.

4 Claims, 6 Drawing Figures

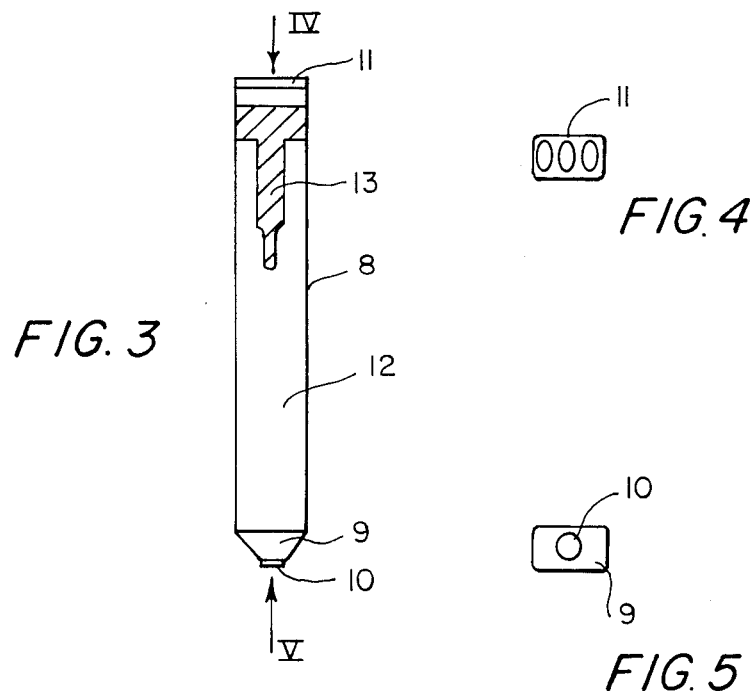
FIG. 3
FIG. 4
FIG. 5
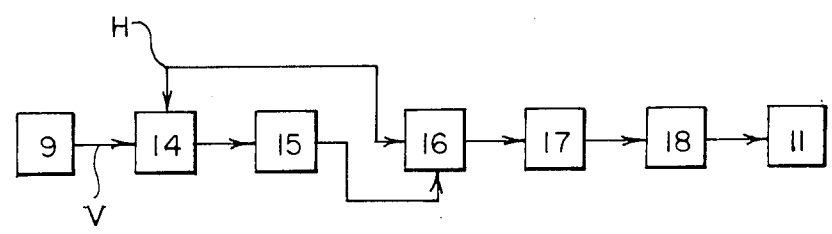
FIG. 6

APPARATUS AND PROCESS FOR VERY RAPIDLY MEASURING THE HEART BEAT RATE

The present invention relates to an apparatus and a process for measuring the rate of heart beat for displaying in two or three seconds the number of contractions effected by the heart in a minute. The conventional procedure for measuring the heart beat rate consists in taking the wrist of the patient in one hand, detecting by touch the pulsatile wave of the blood flow in the radial artery, counting zero while taking a reference mark on the dial of an analog watch or mentally noting the value displayed by a digital display watch at the time of a maximum of the pulsatile wave, counting one at the time of a second maximum of the pulsatile wave, counting two at the time of a third maximum of a pulsatile wave, and so on until a certain time, generally a minute, has elapsed.

A first drawback of this method is that at least a minute is required before knowing the heart beat rate of a patient with relatively good accuracy, and that during this minute the practicioner must not be distracted in any way for that would make him forget his reference mark during the time elapsed or the count of the pulses from the beginning of his observation.

A second drawback of this method is that very often the practicioner, whose is generally in a hurry, only counts the passing of the pulsatile wave for 15 seconds, then he multiplies the number of pulses detected from the beginning of his observation by four. The result is a doubt concerning the determination of the heart beat rate by at least one pulse per 15 seconds, i.e. at least four pulses per minute. If further the practicioner counts 1 instead of zero at the first pulse detected, the result is often an uncertainty of eight pulses per minute.

The aim of the invention is essentially to overcome these disadvantages as far as possible and to allow anyone to measure on himself as readily as on someone else the number of heart beats per minute with a reliability which has been reserved for experienced specialists working in good conditions of tranquility, and that in an extremely short time of two or three seconds.

To these ends, the apparatus of the invention comprises:

a force sensor or dynamometer intended to be held in the anatomical gutter of the radial artery, usually called the wrist-pressure point, with a substantially constant force less than that created by the systolic pressure of the blood flow in the radial artery;

detection means connected to said dynamometer and adapted for detecting the maxima of the output signals of the dynamometer;

computing means connected to said detection means and adapted for measuring the duration of the time T separating two maxima of the output signals of the dynamometer, computing its inverse 1/T and multiplying this latter by 60, these computing means having their output connected to display means for displaying, at the end of each heart beat cycle, the frequency or heart beat rate evaluated as a number of pulses per minute of time.

The invention will be better understood from reading the detailed description which follows of the structure and use of a preferred embodiment of an apparatus constructed in accordance with the invention, which preferred embodiment is given solely by way of illustration without any limitative character. In this description, reference is made to the accompanying drawings in which:

FIG. 3 is a profile view of a preferred embodiment of the apparatus of the invention;

FIG. 4 is a front view of the display means of the apparatus (seen along arrow IV in FIG. 3);

FIG. 5 gives a front view of the parts of the apparatus which the user presses in the anatomical gutter of the radial artery (view seen along arrow V in FIG. 3); and FIG. 6 is a block diagram showing the structure of the apparatus of FIGS. 3 to 5.

Figure 1:
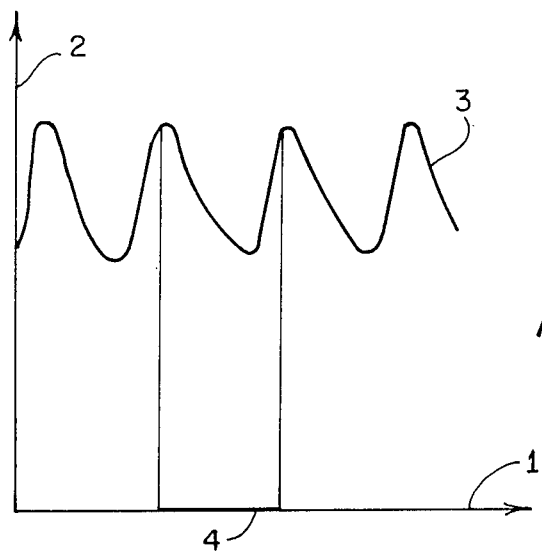
FIG. 1 is a graph giving an example of the evolution of the arterial pressure as a function of time.

FIG. 1 shows the evolution, as a function of current time along axis 1, of one example of four arterial pressure cycles 3 plotted along axis 2. Segment 4 separating two maxima represents the magnitude T of one period of the heart beat cycle. The maxima correspond to the systolic pressure of the blood flow, the minima to its diastolic pressure.

Figure 2:
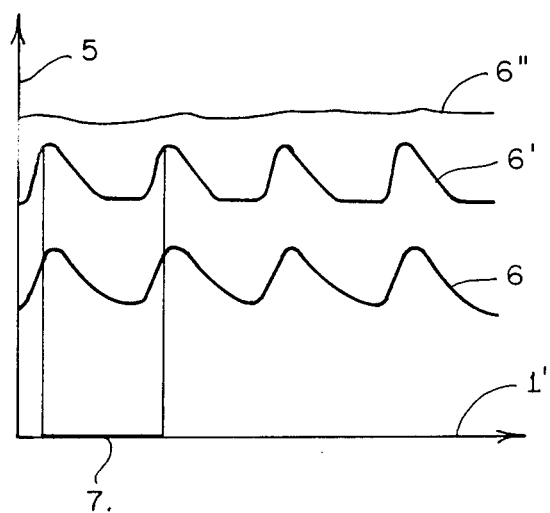
FIG. 2 is a graph giving examples of voltages supplied by the dynamometer as a function of time for three values of the force exerted by the user of the apparatus.

FIG. 2 shows the evolution, as a function of current time along axis 1', of an example of the voltages (expressed in volts) plotted along axis 5 and supplied by the dynamometer used for detecting the pulsatile wave of the arterial pressure.

Voltage 6 is obtained for a pressing force less than that created by the diastolic pressure.

Voltage 6' is obtained for a pressing force greater than that created by the diastolic pressure but less than that created by the systolic pressure.

Voltage 6" is obtained for a pressing force greater than that created by the systolic pressure. This practically constant voltage does not allow the maxima of the pulsatile wave to be detected and this is why the pressing force must be less than that created by the systolic pressure.

It will be noted in FIG. 2 that segment 7 separating two maxima of voltages 6 and 6' is equal to segment 4 of FIG. 1, i.e. to the magnitude T of a period of the heart beat cycle.

FIG. 3 shows a profile view of a preferred embodiment of the apparatus of the invention which has the shape of a parallelepiped 8 with rounded edges which may for example have a length of about 8 cm and a cross section of 8 mm by 12 mm. End 9 is slightly bulging and comprises a contact piece 10 with a diameter of about 5 mm rigidly connected to a membrane of the dynamometer 9' (shown in block diagram FIG. 6). This membrane is preferably made from a conducting silicon and forms, with an internal insulated electrode, a variable capacity modifying the frequency of an oscillator at the same rate as the pulsatile wave travelling through the artery.

The other end 11 is formed by a three digital character display unit.

Body 12 of the apparatus contains one or more electric batteries and the electronic means required for its operation. The electronic means are permanently switched on as soon as the battery or batteries are placed in their housing.

A clip 13 allows the apparatus to be fixed in the pocket of a jacket or smock in the manner of a pen.

FIG. 4 shows the display unit seen from the front. The display 000 shown here is the one which is provided before the apparatus is pressed against the radial artery.

FIG. 5 shows the apparatus seen from below showing the end 9 containing the dynamometer and its contact piece 10.

FIG. 6 shows one example, in the form of a block diagram, of the general structure of a preferred embodiment of the apparatus of the invention and of the succession of operations carried out on the voltage V provided by the dynamometer 9' on the assumption that this latter gives a DC analog voltage, under the control of clock H, before reaching the display unit 11.

At time t, the voltage V is sampled and digitalized in block 14.

Block 15 detects the maxima of V.

Block 16 accumulates the increments of clock H under the control of the maxima detected by block 15. It then supplies the period T which is inversed and multiplied by 60 in block 17 so as to give the heart beat rate XXX which is fed to the control logic 18 of display unit 11.

The operation of the apparatus of the invention will be readily understood from the following description of its use.

When the apparatus is not pressed against the radial artery, the signal from the dynamometer is zero and there is neither maximum nor minimum; the display unit indicates then 000.

When the apparatus is pressed against the radial artery in the the anatomical gutter of the radial artery with a slight and substantially constant force such as when the practicioner takes the pulse with his fingers, the signal of the dynamometer is automatically analyzed that is to say that the following operations take place successively, a first maximum is detected, the internal timer of the apparatus is set going, a second maximum is detected, the timer is stopped which then gives the value of the period T, 1/T is calculated and multiplied by 60, and this result is displayed which is the number of pulses per minute or the heart beat rate. For a pulse equal to or greater than 60 beats per minute, the time for the measurement is at most two seconds. This time may reach three seconds for a pulse between 60 and 40 beats per minute.

If the apparatus remains pressed against the radial artery, as soon as a third maximum is detected the display unit indicates a new value of the heart beat rate which is obviously identical to the preceding one if the pulse is stable but which is different in the case of arhythmia.

When the apparatus is removed from the radial artery the last heart beat rate displayed continues to appear for about a minute, then the display unit again indicates 000.

It is obvious for a man skilled in the art that the dynamometer used will preferably supply digital information and that this information will be advantageously processed in semiconductor circuits of the microprocessor type widely used today.

It is also evident for a man skilled in the art that numerous modifications may be made to the apparatus of the invention concerning for example the type of dynamometer, the manner of processing its signal, the presentation or shape of the apparatus whose display unit 11 or body 12 may be fitted to the end of a cord, may transmit the measurement over a certain distance or may be replaced by a speaking device, without departing from the scope of the invention.

Consequently, the invention should not be interpreted as being limited to the particular embodiment described here, it covers on the contrary all variants thereof.

We claim:

1. An apparatus for very rapidly, externally measuring the heart beat rate of a patient comprising:
   a housing having a tip portion to which is mounted a slightly bulging contact piece extending beyond said housing for being placed in direct contact with the wrist blood pressure point of the patient;
   at least one dynamometer located in said housing tip which receives mechanical input signals when said contact piece is placed in operative contact with the pressure point of the patient and thereby transfers the contact to said dynamometer which converts said mechanical input signals to electrical signals with a force that is relatively constant and less than the force created by the systolic pressure of the blood flow in the radial artery of the patient;
   detection means connected to said dynamometer output for detecting the maxima of the said dynamometer signals;
   computing means connected to said detection means for providing an electrical signal indicative of the heart beat rate, said computing means comprising:
   means for determining two maxima,
   means for calculating the period T separating two maxima,
   means for calculating the inverse of said period, and
   means for converting said inverse period to a time unit and for providing the result at an output thereof; and
   visual, numeric display means for displaying said result as a number.

2. Apparatus as claimed in claim 1 and further comprising an elongate case having substantially the appearance of a pen and to which is mounted all the other components.

3. Apparatus as claimed in claim 2 wherein said dynamometer is located at one end of said case and said display means is located at the other end of said case such that the display therefrom is visable from the outside of said case.

4. Apparatus as claimed in claim 2 wherein said case includes a clip for attaching said apparatus in a pocket.

* * * * *